United States Patent
Takekoshi et al.

(10) Patent No.: US 6,218,837 B1
(45) Date of Patent: Apr. 17, 2001

(54) MAGNETIC RESONANCE IMAGING SYSTEM

(75) Inventors: Isamu Takekoshi, Tokyo; Masahito Saegusa, Amagasaki; Mitsuru Ohnuma, Tokyo; Atsushi Ninomiya, Ome; Atsushi Katayama, Kokubunji; Shigeru Sato, Ibaraki-ken; Tsuneo Maeda, Tokyo, all of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/429,952

(22) Filed: Oct. 29, 1999

Related U.S. Application Data

(62) Division of application No. 08/560,388, filed on Nov. 17, 1995, now Pat. No. 6,049,208.

(30) Foreign Application Priority Data

Nov. 25, 1994 (JP) .................................................. 6-290939

(51) Int. Cl.$^7$ ........................................................ G01V 3/00
(52) U.S. Cl. ............................................. 324/319; 324/320
(58) Field of Search ............................... 324/318, 319, 324/320, 321, 307, 309, 300; 600/410, 415, 421

(56) References Cited

U.S. PATENT DOCUMENTS

| | | | |
|---|---|---|---|
| D. 283,729 | 5/1986 | Ramsey | D24/1.1 |
| D. 300,849 | 4/1989 | Steinhilber | D24/2 |
| D. 313,073 | 12/1990 | Kaufman et al. | D24/2 |
| D. 325,632 | 4/1992 | Kogane et al. | D24/158 |
| D. 347,063 | 5/1994 | Ariyoshi et al. | D24/159 |
| 4,629,989 | 12/1986 | Riehl et al. | 324/318 |
| 4,829,252 | 5/1989 | Kaufman | 324/309 |
| 4,943,774 | 7/1990 | Breneman et al. | 324/318 |
| 5,153,546 | 10/1992 | Laskaris | 335/216 |
| 5,305,749 | 4/1994 | Li et al. | 128/653.2 |
| 5,517,121 | * 5/1996 | Kaufman et al. | 324/319 |
| 5,539,314 | * 7/1996 | Arakawa et al. | 324/318 |
| 6,049,208 | * 4/2000 | Takekoshi | 324/319 |

FOREIGN PATENT DOCUMENTS

| | | | |
|---|---|---|---|
| 0314262 | 5/1989 | (EP) . | |
| 6071112 | 5/1985 | (JP) . | |
| 6226052 | 2/1987 | (JP) . | |
| 62295405 | 12/1987 | (JP) . | |
| 1146530 | 6/1989 | (JP) . | |
| 1178251 | 7/1989 | (JP) . | |
| 221846 | 1/1990 | (JP) . | |
| 02218344 | 8/1990 | (JP) | A61B/5/55 |
| 5269117 | 10/1993 | (JP) . | |
| 678893 | 3/1994 | (JP) . | |
| 6261876 | 9/1994 | (JP) . | |
| 917455 | 11/1991 | (WO) . | |

OTHER PUBLICATIONS

"A Monthly Medical Care" Jun. 1992, No. 210, published Jun. 1, 1992, by M.E. promoting Association, pp. 76–78.

\* cited by examiner

*Primary Examiner*—Louis Arana
(74) *Attorney, Agent, or Firm*—Antonelli, Terry, Stout & Kraus, LLP

(57) ABSTRACT

A magnetic resonance imaging system includes a lower body which has a flat upper surface, and contains a first magnetic pole, an upper body which has a lower surface disposed in opposed relation to the upper surface of the lower body, and contains a second magnetic pole, a bed disposed adjacent to the lower body, and a pair of support posts which are provided respectively on right and left sides of the lower body, and interconnect the lower body and the upper body. A space, formed between the lower surface of the upper body and the upper surface of the lower body, is open at least toward the bed between the pair of right and left support posts.

25 Claims, 7 Drawing Sheets

MAGNETIC RESONANCE IMAGING SYSTEM

This is a divisional application of Ser. No. 08/560,388, filed Nov. 17, 1995 now U.S. Pat. No. 6,049,208.

BACKGROUND OF THE INVENTION

1. Field of the Invention

This invention relates generally to a magnetic resonance imaging system (hereinafter referred to as "MRI system"), and more particularly to a MRI system in which considerations, contributing to easy handling, are given to the subject to be examined (hereinafter referred to as "patient"), and also the efficiency of operations, such as a medical treatment to be given to the patient by a doctor, and an examination operation to be effected by a technician or the like (The doctor and the technician will hereinafter be referred to as "doctor or the like"), is improved.

2. Description of the Related Art

A MRI system utilizes nuclear magnetic resonance (NMR) phenomena to provide an image of a cross-sectional area of that portion of the patient to be examined for diagnostic purposes. In such a MRI system, in order to produce NMR phenomena on the patient's portion to be examined, it is necessary to produce a strong magnetic field and then to locate the patient's portion to be examined in this magnetic field.

In conventional MRI systems, generally, a bore such as a tunnel is formed in a strong magnetic field, and the patient is put into this bore. In such a system, although the strong magnetic field can be easily formed, the patient must be loaded into the narrow bore, which has invited a problem that the examination can not be carried out easily. Japanese Patent Unexamined Publication No. 62-26052 discloses a MRI system not using a tunnel space, in which one side of a measurement space is open.

In the conventional MRI systems, the measurement space is formed in the tunnel, or is open at its one side with the remaining sides closed by walls. Therefore, when the patient is inserted into the measurement space for examination purposes, he tends to feel oppressed and uneasy, and it has often been difficult to properly examine the patient of claustrophobia. Moreover, the doctors or the like have now more and more wished to give a medical treatment to the patient simultaneously with the examination operation, and particularly when the patient is an emergency one, it is necessary to effect a medical treatment simultaneously with the examination. In such a case, the doctors or the like need to gain access to the patient from the opposite sides of the patient. With the conventional MRI systems, however, it has been impossible to achieve this.

SUMMARY OF THE INVENTION

It is an object of the present invention to provide a magnetic resonance imaging system capable of decreasing oppressed or uneasy as felt in patients to be examined during examination. And, it is another object of the present invention to provide the magnetic resonance imaging system in which doctors or the like can effect an operation of the examination in easy or a medical treatment at the same time during the examination.

In order to achieve such objects of the present invention, there is provided a magnetic resonance imaging system including a lower body which has a flat upper surface and contains a first magnetic pole, an upper body which has a flat lower surface disposed in opposed relation to the upper surface of the lower body and contains a second magnetic pole, the lower body and the upper body forming an examination space, and a pair of support posts which are provided respectively on sides of the examination space, i.e. both side surfaces of the lower body, these support posts interconnecting the lower body and the upper body, the examination space being open at least toward a bed between the pair of support posts.

And, in order to achieve further the above objects according to the present invention, the support posts are located outside the lower body, the support posts are fixed to the side surfaces of the lower body which extend toward a rear side thereof from a connecting portion of the lower body and the bed, and a space is provided for capable of effecting a medical treatment at the same time during the doctor's examination according to the necessity at the side surfaces thereof between the support posts and the connecting portion of the lower body.

DESCRIPTION OF THE PREFERRED EMBODIMENTS

One preferred embodiment of the present invention will now be described with reference to FIGS. 1 to 3.

Figure 1:
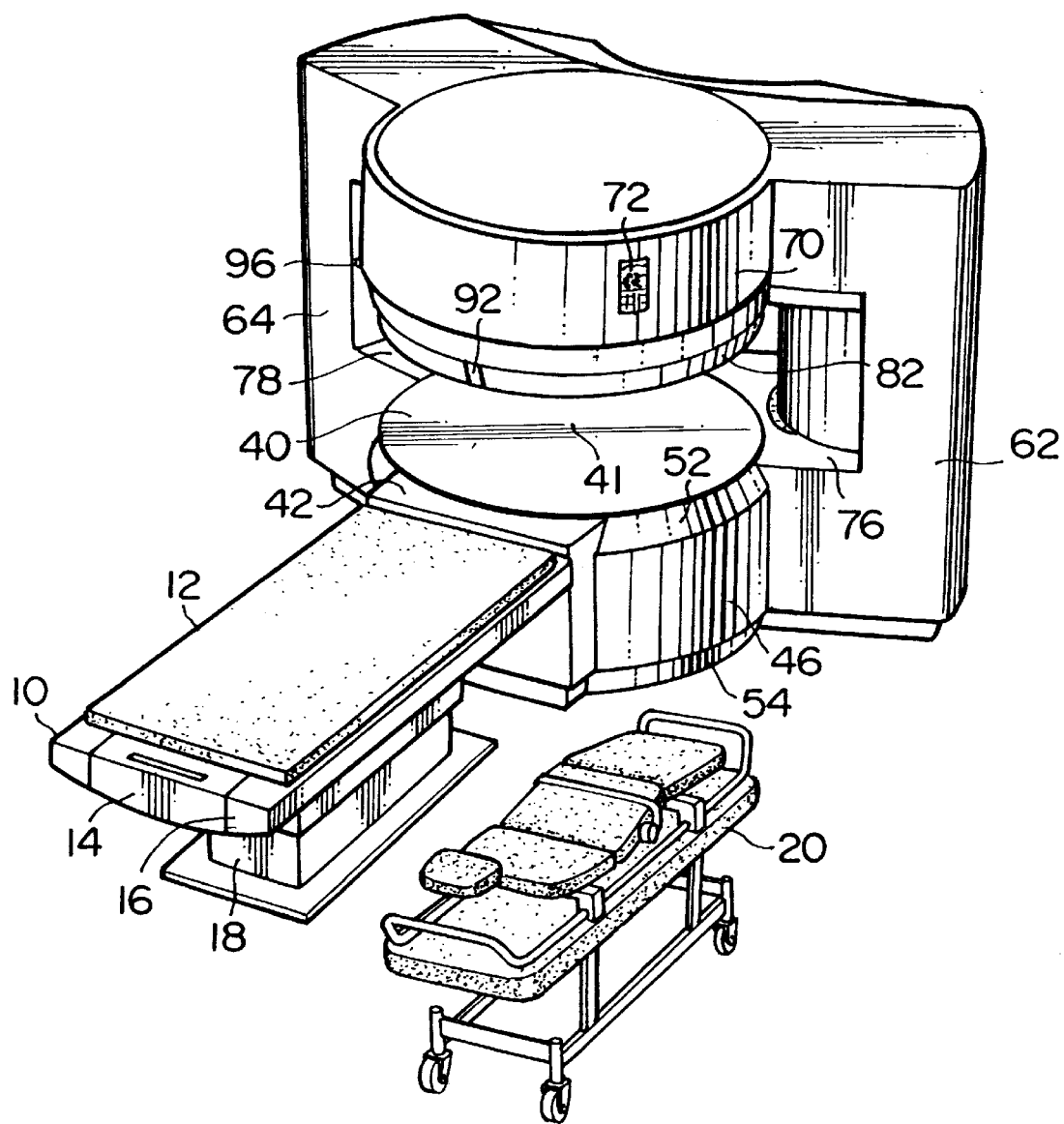
FIG. 1 is a perspective view of a MRI system in accordance with an embodiment of the present invention as seen at an angle from the front side thereof.
Figure 2:
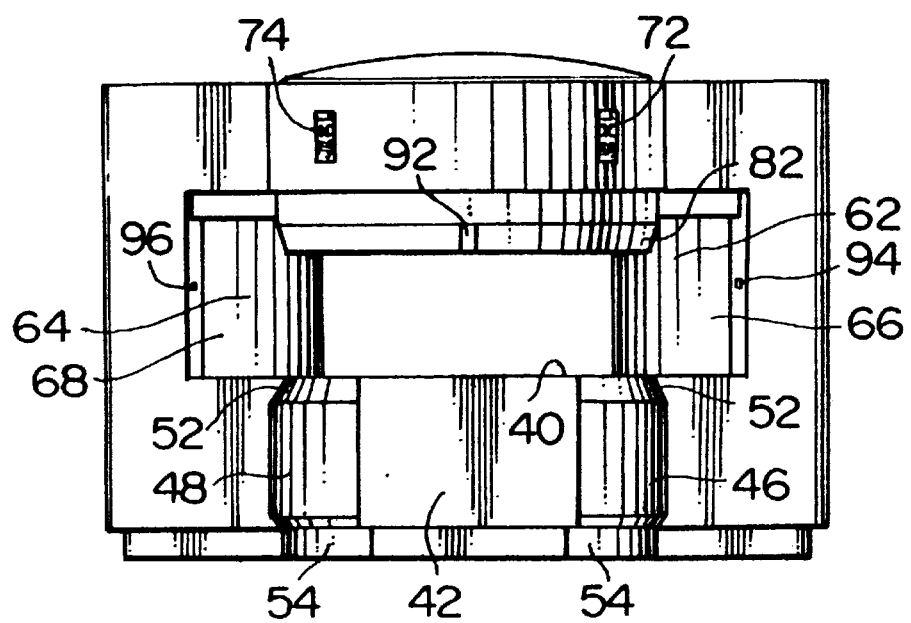
FIG. 2 is a front-elevational view of the MRI system body.

FIG. 1 is a perspective view of a MRI system of the invention as seen at an angle from the front side thereof. A body of this MRI system includes a lower body 40 having a substantially circular upper surface, an upper body 70 which is disposed above the lower body 40, and has a substantially circular lower surface, a pair of opposed right and left support posts 62 and 64 which interconnect the lower body 40 and the upper body 70 in such a manner that the lower body 40 and the upper body 70 are disposed generally between the two support posts 62 and 64. At a front side of the MRI system body of FIG. 1, that is, at one side of the two support posts 62 and 64, a bed 10 is disposed adjacent to the lower body 40 through a connecting portion 42. In this MRI system, the patient is placed on the bed 10, and is transferred or loaded to the lower body 40. In the lower body 40, an examination is effected using known magnetic resonance phenomena, and results of the examination are displayed as an image in a display portion of a central operating device (not shown).

The bed 10 includes a bed body 14, a top plate 12 mounted on the bed body 14, and a bed leg 18. The top plate 12 is driven to move in longitudinal and transverse directions of the bed 10 by a drive device contained in the bed 10. A pair of bed side portions 16, made of a soft material, such as foamed urethane, sponge or rubber, are provided at opposite lateral sides of the bed body 14, respectively, and these bed side portions 16 prevent the patient from injury while he moves onto the bed, and also absorb an impact force produced when a stretcher, on which the patient is placed, is brought into contact with the lateral side of the bed 10. After the patient is placed on the bed 10, the top plate 12 is moved forward, backward, right and left, so that the patient can be accurately loaded to the lower body 40. This operation can be carried out by any one of a pair of operating devices 72 and 74 which are mounted respectively on right and left portions of a front side of an outer peripheral surface of the upper body 70 facing the bed 10, a rear operating device 75 which is mounted on the rear side of the outer peripheral surface of the ceiling portion 70, and the central operating device (See FIGS. 1 to 3). The leg 18 of the bed 10 is much smaller in cross-sectional area than the bed body 14, and is disposed at a central portion of the bed body 14, and the outer periphery of the leg 18 is sufficiently recessed inwardly from the outer periphery of the bed body 14, thus providing a sufficient space at the feet of the doctors or the like that the they can move freely around the bed. This facilitates the examination operation.

Figure 6:
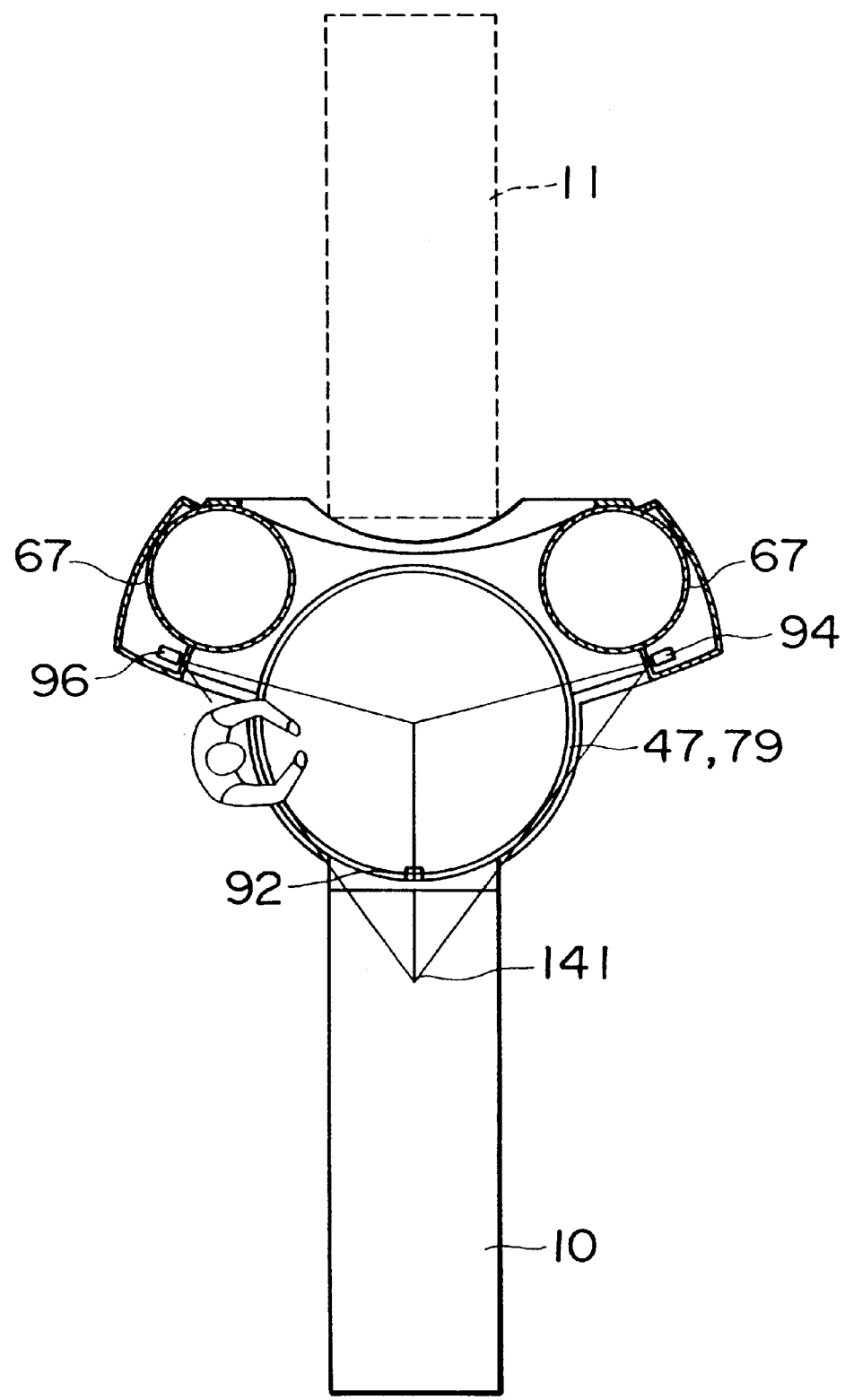
FIG. 6 is a plan view of the MRI system showing the doctor or the like effecting the examination operation at the lateral side thereof.

The upper surface of the lower body 40 is disposed in opposed relation to the lower surface of the upper body 70, and the lower body 40 and the upper body 70 contain respective opposed inclined magnetic field coils, irradiation coils, receiving coils and magnetic poles, and circular yokes 47 and 79 for these parts are also contained respectively in the lower body 40 and the upper body 70, as shown in FIG. 6. The lower body 40 has the bed connecting portion 42 formed at a central portion of the front side thereof for connection to the bed 10. A pair of outer peripheral surfaces (arcuate surfaces) 46 and 48 of the lower body 40, which lie between one end of the bed connecting portion 42 and the right support post 62 and between the other end of the bed connecting portion 42 and the left support post 64, respectively, are substantially part of a cylindrical surface having its axis disposed on an axis 41 of the lower body 40. With this construction, the doctor or the like can move the patient from either of the right and left outer peripheral surfaces 46 and 48 according to the need, and also when the patient to be examined requires the attendance of a nurse or a medical treatment, a necessary medical instrument, such as an oxygen mask and an instillator, can be applied to the patient from the right and left outer peripheral surfaces 46 and 48. The lower body 40 has a circular shape, and that surface of the bed connecting portion 42 facing the bed 10 is straight so as to accurately connect the circular lower body 40 to the bed and also to lessen the burden on the patient during transfer of the patient to the lower body 40.

An upper peripheral edge of the lower body 40 is chamfered or cut off to provide a chamfered or beveled portion 52. The chamfered portion 52 is made of a soft material. With this construction, the doctors or the like and the patient are prevented from being injured by the upper edge of the lower body 40, and also the doctors or the like can easily approach the patient. A lower peripheral edge portion of the lower body 40 is recessed as at 54, thus providing a space at the feet of the doctors or the like so that they can easily move around the lower body 40 during the examination and a medical treatment.

The front side (surface) and opposite lateral sides (surfaces) of the upper body 70 continuous therewith are defined by a substantially semi-circular surface, and therefore the degree of opening of an measurement space is high, so that the patient feels less oppressed. In addition, because of this widely-open arrangement, the doctors or the like can effect the operation easily. A lower peripheral edge of the upper body 70 is chamfered or cut off to provide a chambered or beveled portion 82, and this chambered portion 82 is made of a soft material. With this construction, even if the doctors or the like hit their head against this edge during the operation, they will not be injured.

The lower body 40 and the upper body 70 are interconnected by the pair of right and left support posts 62 and 64 provided respectively on opposite (right and left) sides of the lower body 40 and the upper body 70 as seen from the bed 10 (FIG. 1) in such a manner that the lower body 40 and the upper body 70 are interposed between the two support posts 62 and 64. A magnetic circuit is formed in these support posts 62 and 64, and is connected to the magnetic poles provided respectively within the lower body 40 and the upper body 70. A circular yoke 67 is contained in each of the two support posts 62 and 64, as shown in FIG. 6. The right and left support posts 62 and 64 are spaced apart from the lower body 40, so that a space is formed between the outer periphery of the lower body 40 and the outer periphery of each of the two support posts 62 and 64. As a result, a space 66 is formed between the inner side of the right support post 62 and the outer periphery of the measurement space formed between the lower body 40 and the upper body 70 whereas a space 68 is formed between the inner side of the left support post 64 and the outer periphery of the measurement space. The support posts 62 and 64 are formed into a generally square cross-section, so that extension portions, which constitute side tables 76 and 78, respectively, are formed respectively at the bottoms of these spaces 66 and 68. With this construction, the patient placed on the lower body 40 can feel easy, and also when applying a medical treatment to the patient, medical instruments can put on the side tables 76 and 78, and the doctors or the like can effect the operation easily. Illumination means 61 and 63 can be provided respectively on the inner sides of the right and left support posts 62 and 64 respectively facing the spaces 66 and 68, or on the side tables 76 and 78, respectively. In this case, the space is made brighter, so that the patient can feel less oppressed, and also the doctors or the like can effect the operation more easily, which prevents errors in the operation. The right operating device 72 is provided in the outer peripheral surface of the upper body 70, and is disposed between the front side thereof which faces the bed 10 and the right support post 62, whereas the left operating device 74 is provided in the outer peripheral surface of the upper body 70, and is disposed between the front side thereof and the left support post 64. Further, the rear operating device 75 is provided in the rear surface of the upper body 70 lying between the two support posts 62 and 64, as shown in FIG. 3. With this arrangement, the doctor or the like, even if positioned at any of the right, left and rear sides of the lower body 40, can effect the operations such as the movement of the bed 10 and the start and interruption of the examination operation.

Figure 3:
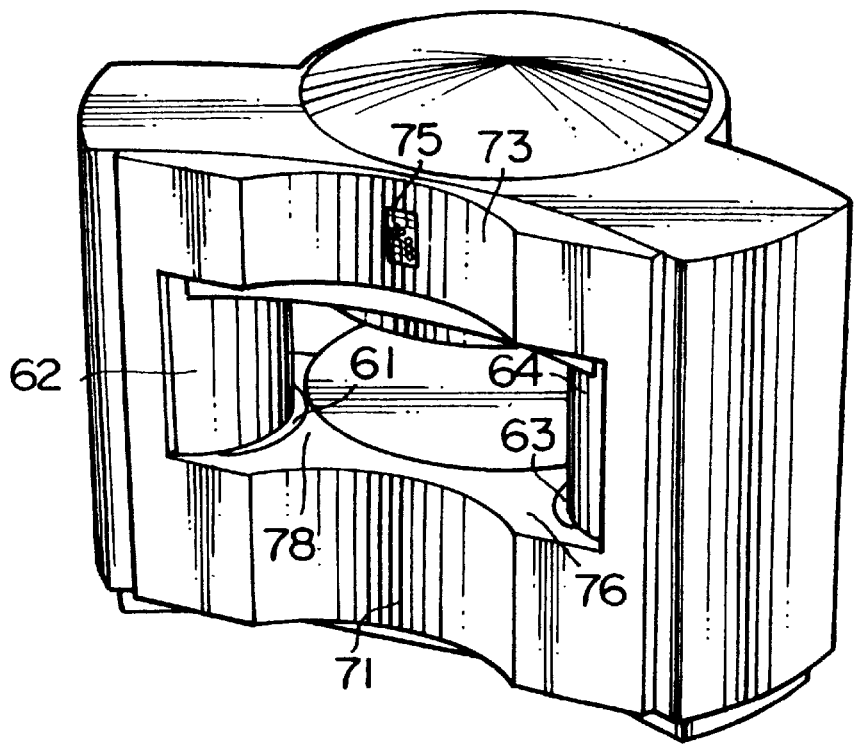
FIG. 3 is a perspective view of the MRI system body as seen at an angle form the rear side thereof.

The space, formed by the lower body 40 and the upper body 70, is also wide open at the rear side as shown in FIG. 3. This open construction is obtained by recessing the rear sides of the lower body 40 and the upper body 70 over a wide range between the two support posts 62 and 64. More specifically, a recess 71 is formed in the rear side of the outer periphery of the lower body 40, and a recess 73 is formed in the rear side of the outer periphery of the upper body 70. With this construction, the distance from the rear side to the center of the lower body 40 is reduced, so that the operation can be effected easily in the measurement space.

In the above embodiment, as shown in FIG. 6, the support posts have the surfaces not opposed to the lower body as formed as large curved surfaces. Although it is described above that the support posts have a generally square crosssection, all the side surfaces thoseof may be made straight, the crosssections may be square, and all corner portions of the support posts may be cut off.

A central light marker 92 is mounted on the front side of the cut portion 82 provided in the outer peripheral surface of the upper body 70 adjacent to its lower surface, and a pair of side light markers 94 and 96 are provided on the side surfaces of the right and left support posts at the sides of the examination space 62 and 64, respectively. These light markers 92, 94 and 96 emit light beams serving as a reference of the positional relation.

Figure 4:
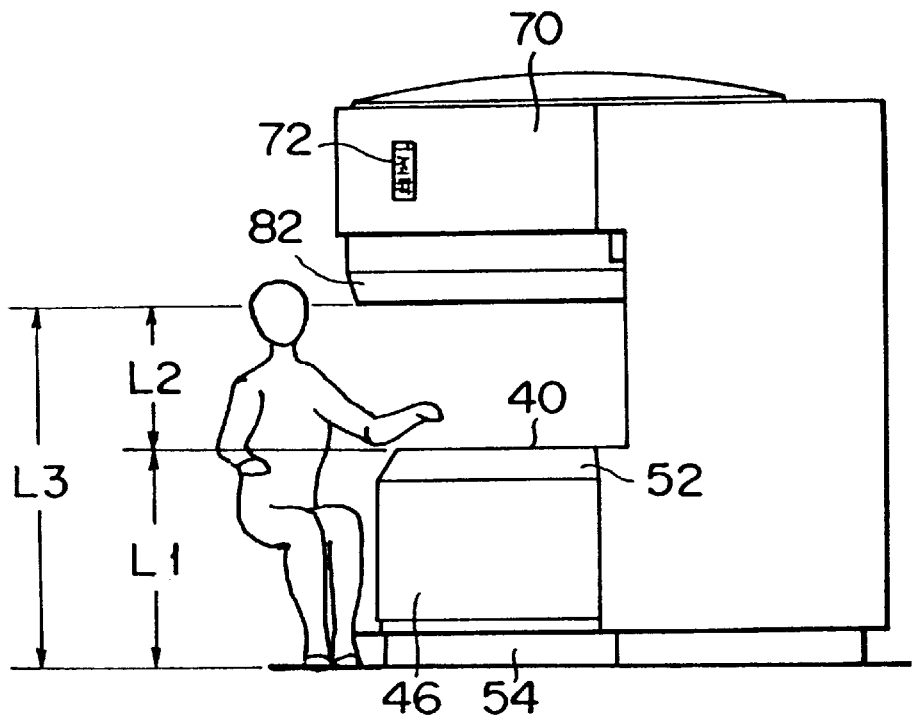
FIG. 4 is a side-elevational view of the MRI system, showing the doctor or the like effecting an examination operation while sitting on a chair.

FIG. 4 is a view showing the doctor or the like conducting the examination while sitting on a chair. A height L1 of the upper surface of the lower body 40 is in the range of between 600 mm and 800 mm so that the doctor or the like can put his head into the measurement space formed between the upper surface of the lower body 40 and the lower surface of the upper body 70. A height L3 of the lower surface of the upper body 70 from a floor surface on which the lower body 40 is mounted is set to 1,285 mm in this embodiment. Preferably, this height L3 is in the range of between 1,000 mm and 1,550 mm. In order to enhance the resolution of the image obtained as the examination result, it is desirable that the distance or spacing between the upper surface of the lower body 40 and the lower surface of the upper body 70 be small, and for this reason the height L3 is set to 1,285 mm. A vertical dimension L2 of the measurement space between the upper surface of the lower body 40 and the lower surface of the upper body 70 is in the range of between 350 mm to 435 mm. With this value, the patient, lying down on the lower body 40, can move both hands, and if this dimension is increased, the patient can move his hands more easily, but the precision of the examination is lowered.

Figure 5:
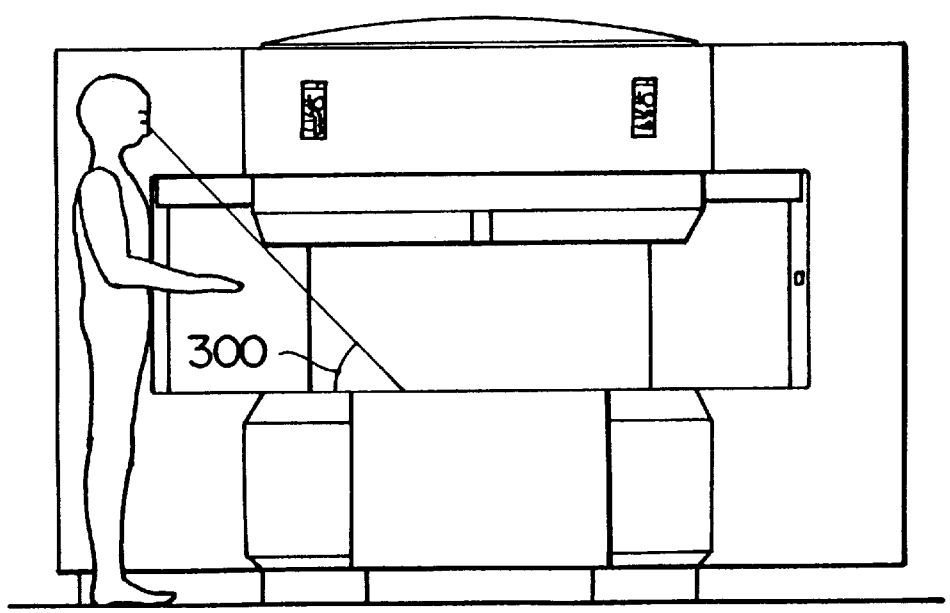
FIG. 5 is a front-elevational view of the MRI system showing the doctor or the like effecting the examination operation at a lateral side thereof.

The lower body 40 has the chambered portion 52 formed at the upper peripheral edge thereof, and the upper body 70 has the chamfered portion 82 formed at the lower peripheral edge thereof. Therefore, the doctors and other attending personnel are prevented from being injured upon striking against these edges. The recess 54 is formed at the lower peripheral edge portion of the lower body 40, and therefore the nails of the foot of the doctor or the like will not strike against this lower end. FIG. 5 is a view showing the doctor or the like effecting the operation while standing up at the lateral side of the lower body 40. Since the lower peripheral edge of the upper body 70 is cut off or chamfered, the doctor or the like can better look into the measurement space above the lower body 40, so that the operation can be carried out easily. The lower peripheral edge of the upper body 70 may be chamfered over the entire periphery thereof to provide the chamfered portion 82 either in such a manner that the outer peripheral surface thereof is straight in transverse cross-section as indicated at the left of FIG. 5, or in such a manner that the outer peripheral surface is rounded in transverse cross-section as indicated by a broken line at the right. In FIG. 5, preferably, an inclination angle 300 is in the range of between 40° and 75°. In the case where the chambered portion 82 has the rounded peripheral surface, the radius of curvature thereof is preferably in the range of between 50 mm and 80 mm. As shown in FIGS. 1 and 3, the upper surface of the upper body 70 is flat at its outer peripheral portion, and the remainder surrounded by this outer peripheral portion is slightly outwardly convex to assume a dome-like configuration, thereby increasing the strength.

FIG. 6 is a view showing the doctor or the like standing up at the lateral side of the lower body 40. The center or axis 41 of the lower body 40 coincides with the center of the measurement space, and it is preferred that portion of the patient to be examined should be disposed on this center 41. In this condition, the doctors or the like can be positioned accurately at the opposite sides of the lower body 40, and hence at the opposite sides of the patient, respectively, and therefore the various operations can be carried out efficiently. The light markers 92, 94 and 96 accurately indicate a reference position 141 of the bed and the reference position 41 of the measurement space by light beams emitted therefrom. The patient is properly positioned by the reference position 141 of the bed 10, and then is automatically moved or transferred into the reference position in the measurement space. At this time, however, if the patient moves himself, a deviation results from this movement. In this case, the doctors or the like must again position the patient with respect to the reference position in the measurement space; however, since the light markers 92, 94 and 96 can indicate the position of the center of the measurement space, the position of the patient can be easily corrected accurately.

Figure 7:
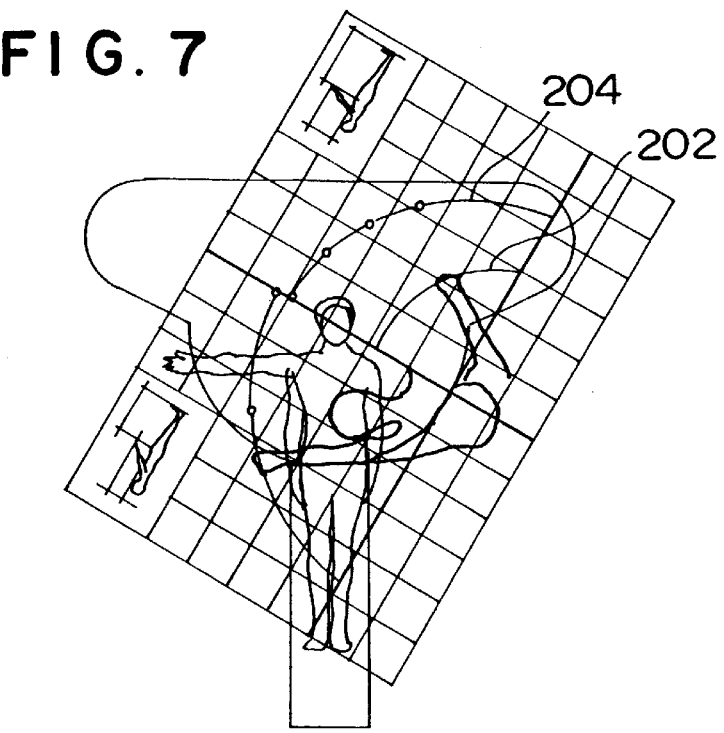
FIG. 7 is a plan view showing the range of the examination operation effected by the doctor or the like at the lateral side of the MRI system.

FIG. 7 is a view showing an area of the operation to be effected by the doctor or the like standing up at the lateral side of the lower body 40. If the height of the lower body 40 is 1,000 mm, the doctor or the like can effect the operation in the range of an operation line 202, that is, in the range of 600 mm from the doctor or the like. If the height of the lower body 40 is about 800 mm, the operation range is increased to the range of an operation line 204, that is, in the range of 1,000 mm from the doctor or the like. In this embodiment, the height of the lower body 40 is in the range of between 600 mm and 750 mm, the operation range is increased. In the above embodiment, the hands can reach deeper beyond the center of the lower body 40, so that the various operations can be dealt with.

Figure 8:
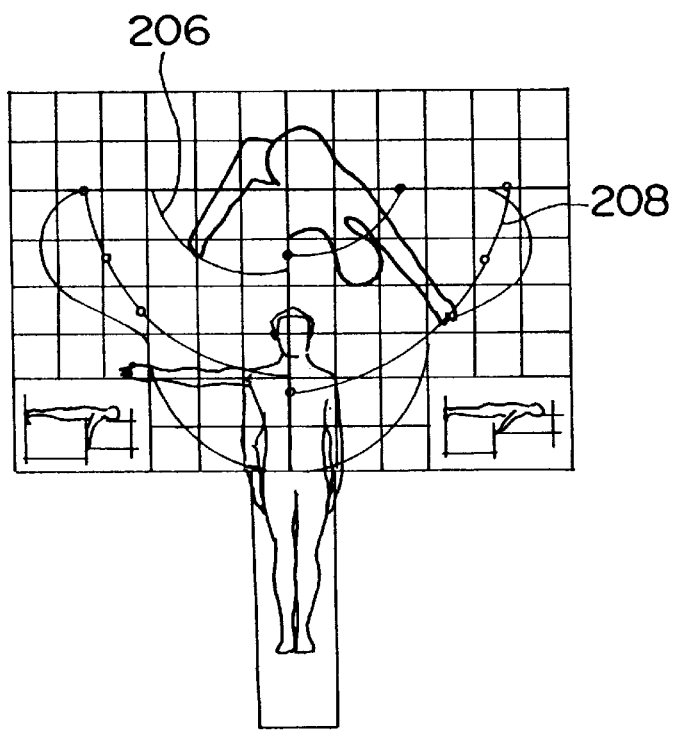
FIG. 8 is a plan view showing the range of the examination operation effected by the doctor or the like at the rear side of the MRI system.

FIG. 8 is a view showing the doctor or the like effecting the operation while standing up at the rear side of the lower body 40. If the height of the lower body 40 is 1,000 mm, the operation range is in the range of an operation line 206, that is, in the range of 600 mm from the doctor or the like, as described above for FIG. 7. If the height of the lower body 40 is about 800 mm, the operation range is increased to the range of an operation line 208, that is, in the range of 1,000 mm from the doctor or the like. In this embodiment, height of the lower body 40 is in the range of between 600 mm and 750 mm as explained for FIG. 7, the operation can be effected in the range of the operation line 208, that is, in the range of 1,000 mm from the doctor or the like. Since the rear side is concave inwardly as shown in FIG. 8, the operation range is further increased.

Furthermore, the above L1 is desirable to be made the value between 600 mm and 750 mm in case of the patient to be examined lying on the lower body for examination and further desirable to be the value between 600 mm and 800 mm in case of the doctor or the like operating while sitting on a chair or standing up.

And, the above L2 is desirable to be made the value between 400 mm and 435 mm as a dimension thereof for not reducing an accuracy of the examination and in such a manner that the patient to be examined can lie with a space on the lower body. Since the accuracy of the examination can be improved by setting the height dimension thereof lower value, the L2 is further desirable to be made the value between 350 mm and 435 mm.

Furthermore, the above L3 is most desirable to be made the value between 950 mm and 1235 mm when the most suitable values of the above L1 and L2 are taken into consideration.

Figure 9:
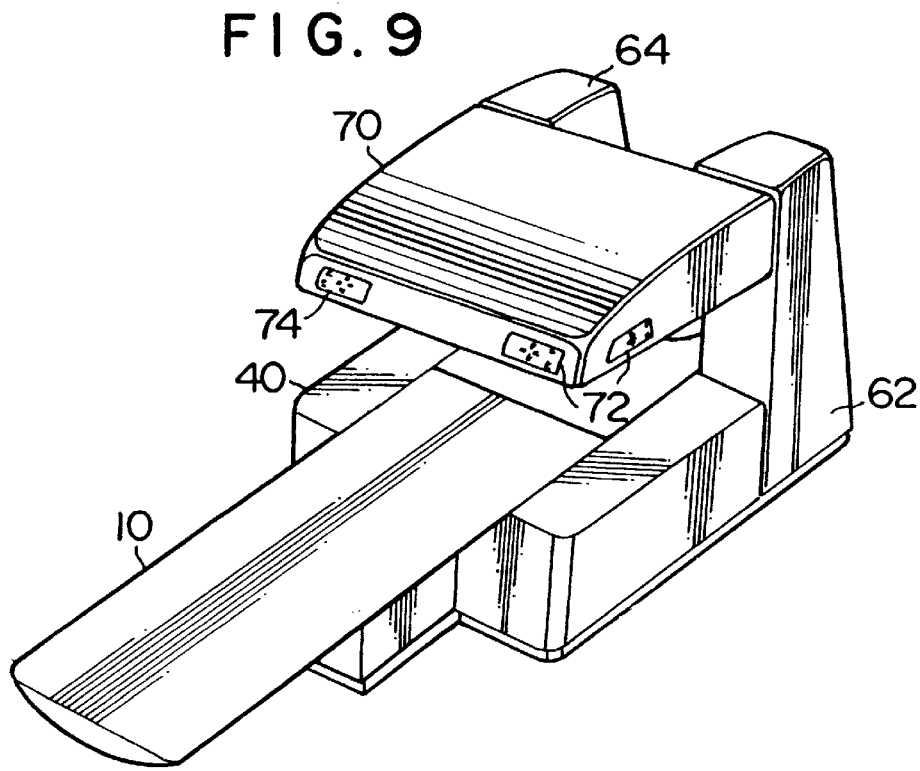
FIG. 9 is a perspective view of a MRI system in accordance with another embodiment of the present invention.
Figure 10:
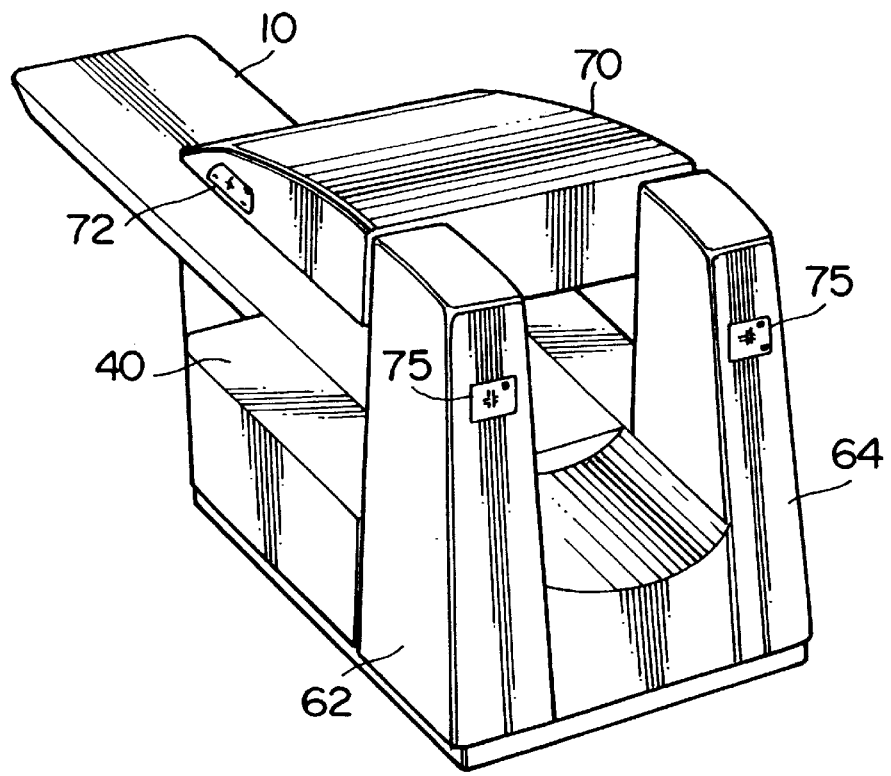
FIG. 10 is a perspective view of the MRI system of FIG. 9 as seen from the rear side thereof.

FIGS. 9 and 10 show a MRI system according to another embodiment of the present invention. A front portion of a lower body 40 is connected to a bed 10 in continuous relation thereto. A pair of opposed right and left support posts 62 and 64 are provided at the rear side of the lower body 40 facing away from the bed 10, and the lower body 40 and an upper body 70 are interconnected by the right and left support posts 62 and 64. The lower body 40 and the upper body 70 contain respective opposed magnetic poles, inclined magnetic field coils, irradiation coils, receiving coils and yokes, as described above in the preceding embodiment. These magnetic poles are electromagnetically connected together through a magnetic circuit formed in the right and left support posts 62 and 64. Opposite lateral sides of the lower body 40 are open, so that the doctors or the like can make an examination of the patient, and can apply a necessary medical treatment to the patient in a manner as described above in the preceding embodiment. The distance between each of the opposite sides of the lower body 40 and the center thereof is 750 mm. Preferably, this distance is in the range of between 500 mm and 750 mm. With this range, the hands can reach the patient from the right, left, front and rear sides, so that the medical treatment can be carried out easily. The bed 10 has a top plate so as to easily move or transfer the patient into the lower body 40 as in the preceding embodiment.

The rear side of this system is also open, and the doctors or the like can effect the necessary operation and treatment. In order to make the rear side wide open, the distance between the right and left support posts 62 and 64, that is, between the outer peripheries of the two support posts, is set to 1,010 mm. A front portion of the upper body 70 is reduced in thickness. This is done not only to reduce the weight of the upper body 70 but also to reduce the thickness of the front portion of the magnetic pole so as to make a magnetic distribution of the magnetic pole generally uniform.

Figure 11:
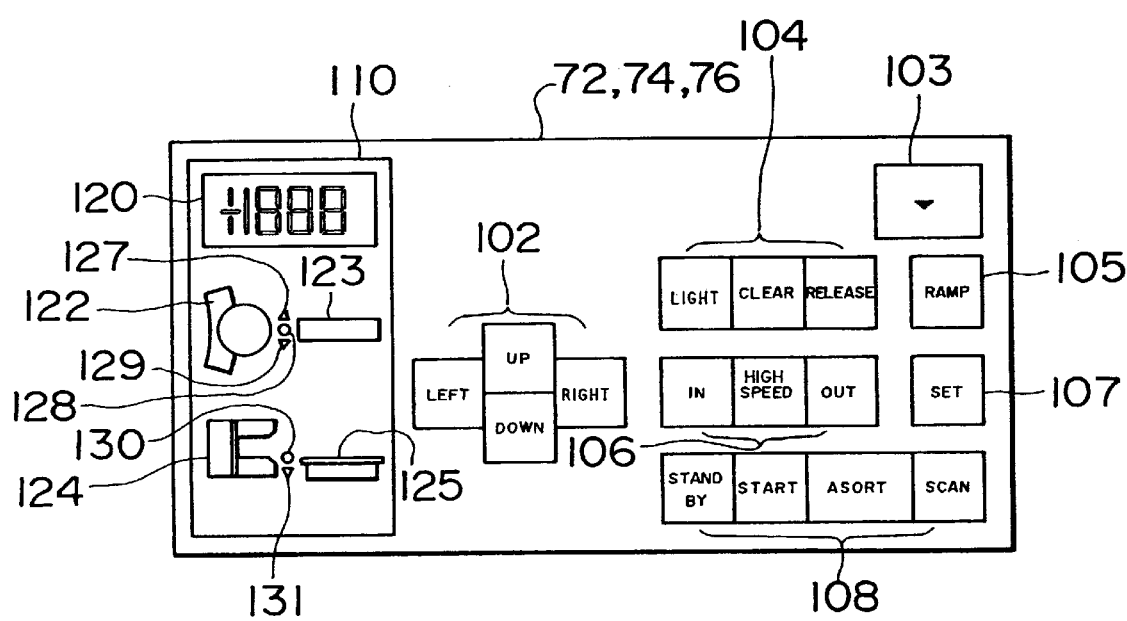
FIG. 11 is a front-elevational view of an operating device used in the MRI system in accordance with the present invention.

FIG. 11 shows details of an operating portion. Positional deviations, that is, deviations in the directions of the width and the height, of the bed from the lower body are numerically displayed on a LED display portion 110. Operation keys 102 are used for operating the bed, and the "LEFT" key and "RIGHT" key are used for moving the bed right and left, and when these keys are operated, indication elements 127 and 129 are lighted to indicate the direction of movement of the bed. When the center of the lower body coincides with the centerline of the bed, an indication element 128 is lighted.

When the "UP" key or the "DOWN" key among the operation keys 102 is operated, the position of a bed 125 in the LED display with respect to a lower body 124 in the LED display in the direction of the height is indicated by indication elements 131 and 130. The indication element 130 is lighted when the height of the bed is generally equal to the height of the lower body, whereas the indication element 131 is lighted when the bed is at a height lower than the lower body, or the bed is in a downward movement mode.

A key 103 is used for indicating emergency stop of the examination operation. Keys 104 are used for turning on an off the light markers and for releasing the setting of indication of the reference position. A key 105 is used for turning on an off the illumination devices. Keys 106 are used for controlling the bed so as to move the patient into and out of the lower body. A key 107 is an automatic control key for loading and unloading the patient. Keys 108 are operation keys for indicating the completion of the preparation for the magnetic resonance operation and for starting the magnetic resonance operation. The above keys are arranged in a predetermined order, and more specifically the operation keys 104 related to the positioning of the patient, as well as the illumination control key 105, are disposed at an upper portion of the operating portion, and the bed operating keys 102, 106 and 107 are disposed next to these keys, and the magnetic resonance operation and scan keys 108 are disposed next to these keys. With respect to the control of the position of the bed, the position of the bed with respect to the lower body is numerically displayed in a display 120 at the left side portion, and the contents of the operation are graphically indicated by the indication elements 127, 129 and 131. Therefore, the contents of the operation can be confirmed, thus preventing an erroneous operation.

In the above embodiments, although the right and left support posts 62 and 64 are offset rearwardly with respect to the center of the lower body 40, these support posts 62 and 64 may be offset forwardly toward the bed. In this case, when a tebet 11 is brought to the lower body, the sense of oppression may slightly increase. However, once it is introduced into the measurement space, the degree of opening of the patient's view is increased, and therefore the patient feels less oppressed during the examination. When the patient requires a medical treatment in addition to the examination, necessary instruments can be brought close to the lower body from the opposite sides and the rear side, since the rear side is wide open during the examination. Therefore, the operation can be carried out easily, and the efficiency of the operation is enhanced.

With the above construction, the doctors or the like can be positioned at the opposite (right and left) sides of the lower body, and the examination can be effected efficiently, and besides the doctors or the like can respond to the patient, and also can apply a necessary medical treatment to the patient, using a medical instrument.

What is claimed is:

1. A magnetic resonance imaging system comprising:
   a lower body having one magnetic pole for generating a magnetic field;
   an upper body having another magnetic pole for generating a magnetic field; and
   a pair of support posts forming a magnetic circuit for passing magnetic flux from one magnetic pole to the other magnetic pole through a first space, said support posts being connected at sides of said lower body and said upper body and symmetrically disposed in a horizontal level thereof,
   wherein said lower body having a first flat surface, a first outer peripheral surface formed on an upper surface thereof and a second outer peripheral surface vertical to said first flat surface, wherein said upper body having a second flat surface, a third outer peripheral surface formed on an upper surface thereof and a fourth outer peripheral surface vertical to said first flat surface, wherein said second flat surface of said upper body is arranged opposite said first flat surface of said lower body and said upper body is formed so that a forward side thereof has an arc-like shape, wherein said fourth outer peripheral surface of said upper body is vertical to and made circular concentric with said second flat surface, wherein said fourth outer peripheral surface of said upper body has a larger diameter than that of said second flat surface, wherein said upper body has an oblique surface made oblique inwardly between said second flat surface and said third outer peripheral surface, and wherein said upper body has at least one operating portion for operating an operation of a bed or an examination.

2. A magnetic resonance imaging system, comprising:

a lower body having one magnetic pole for generating a magnetic field;

an upper body having another magnetic pole for generating a magnetic field; and a pair of support posts forming a magnetic circuit for passing magnetic flux from one magnetic pole to the other magnetic pole through a first space, said support posts being connected at sides of said lower body and said upper body and symmetrically disposed in a horizontal level thereof, wherein said lower body having a first flat surface formed on a first upper surface thereof and second outer peripheral surface vertical to said first flat surface, wherein said upper body having a second flat surface arranged opposite said first flat surface wherein said upper body is formed so that a front side thereof is a circular-arc, wherein said upper body having a third outer peripheral surface vertical to said second flat surface, wherein said third outer peripheral surface of said upper body is form as a circle concentric with said second flat surface and having a diameter larger than that of a circular arc of said second flat surface, wherein said upper body has an oblique surface made oblique inwardly between said second flat surface and said third outer peripheral surface, wherein said oblique surface of said upper body has a light marker provided thereon, and wherein said upper body has at least one operating portion for performing an operation of a bed or examination.

3. A magnetic resonance imaging system according to claim 1, wherein said light marker is disposed on said upper body and said pair of support posts arranged in a horizontal level thereof.

4. A magnetic resonance imaging system according to claim 1, wherein said operation portion for performing an operation of a bed or examination is disposed on said outer peripheral surface of said upper body between said pair of support posts arranged in a horizontal level thereof.

5. A magnetic resonance imaging system according to claim 2, wherein said operation portion for performing an operation of a bed or examination is disposed on said outer peripheral surface of said upper body between said pair of support posts arranged in a horizontal level thereof.

6. A magnetic resonance imaging system according to claim 2, wherein said operation portion provided on said upper body is disposed in neighborhood of said light marker.

7. A magnetic resonance imaging system according to claim 1, wherein said operation portion provided on said upper body is disposed on both sides of said outer peripheral surface of said upper body in view of the bed side.

8. A magnetic resonance imaging system according to claim 2, wherein said operation portion provided on said upper body is disposed on both sides of said outer peripheral surface of said upper body in view of the bed side.

9. A magnetic resonance imaging system according to claim 1, wherein said operation portion provided on said upper body has a displaying portion for displaying a schematic view of positions of said lower body and said bed and displaying vertical and horizontal movement directions of said bed.

10. A magnetic resonance imaging system according to claim 2, wherein said operation portion provided on said upper body has a displaying portion for displaying a schematic view of positions of said lower body and said bed and displaying vertical and horizontal movement directions of said bed.

11. A magnetic resonance imaging system according to claim 9, wherein said displaying portion displays a movement direction of said bed and a difference between the lower body and the bed.

12. A magnetic resonance imaging system according to claim 1, wherein said operating portion provided on said upper body is disposed on said outer peripheral surface of said upper body at an opposite side thereof in view of said bed side.

13. A magnetic resonance imaging system according to claim 2, wherein said operating portion provided on said upper body is disposed on said outer peripheral surface of said upper body at an opposite side thereof in view of said bed side.

14. A magnetic resonance imaging system according to claim 1, wherein said operation portion provided on said upper body has a displaying portion for displaying a positional relation between said lower body and said bed.

15. A magnetic resonance imaging system according to claim 2, wherein said operation portion provided on said upper body has a displaying portion for displaying a positional relation between said lower body and said bed.

16. A magnetic resonance imaging system according to claim 1, wherein said operating portion provided on said upper body has a displaying portion for displaying a vertical relation between said lower body and said bed.

17. A magnetic resonance imaging system according to claim 2, wherein said operating portion provided on said upper body has a displaying portion for displaying a vertical relation between said lower body and said bed.

18. A magnetic resonance imaging system according to claim 1, wherein said operation portion provided on said upper body has a displaying portion for displaying a horizontal relation between said lower body and said bed.

19. A magnetic resonance imaging system according to claim 2, wherein said operation portion provided on said upper body has a displaying portion for displaying a horizontal relation between said lower body and said bed.

20. A magnetic resonance imaging system according to claim 1, wherein said operation portion provided on said upper body has a displaying portion for displaying a difference between central positions of said lower body and said bed.

21. A magnetic resonance imaging system according to claim 2, wherein said operation portion provided on said upper body has a displaying portion for displaying a difference between central positions of said lower body and said bed.

22. A magnetic resonance imaging system according to claim 1, wherein said operation portion has switches for controlling a positional relation between said lower body and said bed.

23. A magnetic resonance imaging system according to claim 2, wherein said operation portion has switches for controlling a positional relation between said lower body and said bed.

24. A magnetic resonance imaging system according to claim 1, wherein said operating portion has a displaying portion for displaying a positional relation between said lower body and said bed with a diagram thereof so as to show a movement direction of said bed.

25. A magnetic resonance imaging system according to claim 2, wherein said operating portion has a displaying portion for displaying a positional relation between said lower body and said bed with a diagram thereof so as to show a movement direction of said bed.

* * * * *